United States Patent [19]

Boardman et al.

[11] Patent Number: 5,260,306
[45] Date of Patent: Nov. 9, 1993

[54] INHALATION PHARMACEUTICALS

[75] Inventors: Terence D. Boardman, Davenham; Raymond B. Forrester, Sandbach, both of England

[73] Assignee: Fisons plc, England

[21] Appl. No.: 727,322

[22] Filed: Jul. 2, 1991

Related U.S. Application Data

[63] Continuation of Ser. No. 403,788, Sep. 6, 1989, abandoned, which is a continuation of Ser. No. 864,807, May 19, 1986, abandoned, which is a continuation-in-part of Ser. No. 606,542, May 3, 1986, Pat. No. 4,590,206, which is a continuation of Ser. No. 399,748, Jul. 19, 1982, abandoned.

[30] Foreign Application Priority Data

Jul. 24, 1981 [GB] United Kingdom ............... 8122846
Mar. 19, 1986 [GB] United Kingdom ............... 8606755

[51] Int. Cl.$^5$ .............................................. A61K 31/44
[52] U.S. Cl. ..................................... 514/291; 514/826; 514/951
[58] Field of Search ........................ 514/291, 826, 951

[56] References Cited

U.S. PATENT DOCUMENTS

| | | | |
|---|---|---|---|
| 3,957,965 | 5/1976 | Hartley et al. | 514/456 X |
| 4,161,516 | 7/1979 | Bell | 514/456 X |
| 4,419,352 | 12/1983 | Cox et al. | 514/291 |
| 4,590,206 | 5/1986 | Forrester et al. | 514/456 |
| 4,760,072 | 7/1988 | Brown et al. | 514/291 |

OTHER PUBLICATIONS

USAN & USP Dictionary of Drug Names, 1986, p. 225.

Primary Examiner—Leonard Schenkman
Attorney, Agent, or Firm—Marshall, O'Toole, Gerstein, Murray & Borun

[57] ABSTRACT

There is described finely divided nedocromil sodium, comprising a therapeutically effective proportion of individual particles capable of penetrating deep into the lung, characterized in that a bulk of the particles which is both unagglomerated and unmixed with a coarse carrier, is sufficiently free flowing to be filled into capsules on an automatic filling machine and to empty from an opened capsule in an inhalation device.

There is also described a method of making the fine particles and pharmaceutical formulations containing them.

18 Claims, No Drawings

INHALATION PHARMACEUTICALS

This application is a continuation, of Ser. No. 07/403,788 filed Sep. 6, 1989; in turn a Cont. of Ser. No. 06/864,807 filed May 19, 1986; in turn a C-I-P of Ser. No. 606,542 filed May 3, 1986 (U.S. Pat. No. 4,590,206 issued May 20, 1986); in turn a Cont. of Ser. No. 399,748 filed Jul. 19, 1982, all abandoned.

This invention relates to a novel form of nedocromil sodium and to methods for its production and formulation.

In our British Patent No. 1,122,284 we have described and claimed an insufflator device for use in the administration of powdered medicaments by inhalation. With that device, and other devices, e.g. that described in British Patent Specification No. 1,331,216, and European Patent Application No. 813021839 a user inhales air through the device which causes a powder container mounted therein to rotate. Powder within the container is fluidised and dispensed into the air stream which is inhaled by the user. For optimum dispensing it has been found that the powdered medicament particles should be comparatively free-flowing and yet should have an ultimate particle size of less than about ten microns to ensure adequate penetration of the medicament into the lungs of the user. These two requirements are prima facie mutually exclusive, since such fine powders are not usually sufficiently free-flowing.

We have now found particles of nedocromil sodium which can penetrate deep into the lung and yet which are sufficiently free flowing to be filled into capsules, and otherwise manipulated, without mixing with a coarse diluent or formation into soft pellets or granules. These particles can disperse well from an inhaler at both low and high air flow rates, thus in certain circumstances, improving consistency of capsule emptying. Furthermore, we have found that these particles can, in general, be coarser than those of the prior art while giving an equivalent proportion of particles which penetrate deep into the lung.

According to the invention we provide finely divided nedocromil sodium comprising a therapeutically effective proportion of individual particles capable of penetrating deep into the lung, characterised in that a bulk of the particles which is both unagglomerated and unmixed with a coarse carrier, is sufficiently free flowing to be capable of being filled into capsules on an automatic filling machine and to empty from an opened capsule in an inhalation device.

With respect to their shape the particles of the present invention are strongly differentiated from the prior art micronised material. The particles may be smooth-surfaced and/or they may be a dented spherical shape and/or of toroidal shape. A low particle density in the material is indicative of fragile particles and is, in general, to be avoided. We prefer the particles to be as uniform as possible in all respects.

The roughness of the surface of the particles can be determined by measuring the total surface area of the particle by the Brunauer, Emett and Teller (BET) method (British Standard 4359 (1969) Part 1) and comparing this with the envelope surface area of the particles as measured by permeametry (Papadakis M. (1963) Rev. Mater. Construct. Trav. 570, 79–81).

We prefer the permeametry: BET ratio to be in the range 0.5 to 1.0, preferably 0.6 to 1.0 and more preferably 0.7 to 0.95 (note a ratio of 1.0 represents a perfectly smooth particle).

We prefer the particles of the invention to be as strong and as dense as possible. The particle density of the particles (as opposed to the bulk density) may be measured by a) the petroleum ether method in which a known weight (25 g) of powder is weighed into a measuring cylinder, a known amount of petroleum ether (50 ml) is added and the mixture shaken until all the powder is suspended. The inner walls of the measuring cylinder are washed with a small amount of petroleum ether (10 ml). Knowing the weight of powder used, the volume of petroleum ether added and the final suspension volume, the particle density can be calculated.

or b) the air pycnometer method in which a given amount of powder is placed in a chamber which is hermetically sealed. The volume of the chamber is gradually reduced by a moving piston until a specified pressure is reached. The position of the piston indicates the volume of the powder particles, hence the particle density can be calculated.

We prefer the particles, of nedocromil sodium, to have a particle density according to the above methods of from about 1.3 to 1.8 and preferably from 1.4 to 1.7 $g/cm^3$.

Micronised nedocromil sodium of the prior art has a loose bulk density of about 0.175 $g/cm^3$ and a packed bulk density of about 0.220 $g/cm^3$. In measuring loose bulk density a suitable amount of powder (40 g) is poured, at an angle of 45°, into a measuring cylinder (250 ml). The volume occupied by the powder in the measuring cylinder when related to the original mass of powder provides the measure of "loose bulk density". If the powder, in the cylinder, is tapped or jolted, e.g. using the Engelsmann Jolting Volumeter, until a stable volume is attained (500 jolts) then the lower volume after jolting when compared with the original mass of powder provides the measure of "packed bulk density".

We prefer the particles of the present invention to have a loose bulk density of greater than about 0.3 $g/cm^3$, preferably of greater than 0.4 $g/cm^3$, more preferably of from 0.5 to 1.0 $g/cm^3$, and most preferably 0.5 to 0.7 $g/cm^3$; and a packed bulk density of from about 0.5 to 1.0 $g/cm^3$ and preferably of from 0.6 to 0.8 $g/cm^3$. The bulk densities of materials are, in general, relatively independent of the particular material used, but are dependent on the shape, size and size distribution of the particles involved.

We prefer the particles of nedocromil sodium when they are intended for administration as a dry powder in, for example, a gelatine capsule to have a moisture content of from 8.0 to 14.0, and preferably from 8.0 to 11.0% w/w. Before filling into the capsule the powder will tend to be at the lower end of the moisture range, and after filling to be at the upper end of the range. Nedocromil sodium powders according to the invention may also be made containing very low, e.g. less than 5%, or preferably less than 4%, w/w, quantities of water. These very dry powders may be used in pressurised aerosol formulations. The water contents in this specification are those measured by Karl-Fischer test.

The individual particles may comprise the active ingredient together with a suitable diluent, e.g. lactose or hydroxypropylmethyl cellulose. The incorporation of the diluent in the particle avoids the possibility of segregation which is possible when individual fine particles of active ingredient are used with separate coarse particles of diluent and it may inhibit the formation of toroidal particles.

We prefer that at least 80% by weight and preferably more than 90%, of the drug particles are of less than 60 microns, more preferably of less than 40 microns, most preferably of less than 30 microns and especially of less than 20 microns, e.g. less than 15 microns in diameter. We particularly prefer at least 80% of the particles to be of 2 to 15 microns in diameter. In general the smaller the mass mean diameter of the material the higher will be the dispersion of the material.

Nedocromil sodium, having a median diameter of from 2 to 18 microns can, because of the enhanced aerodynamic properties of the particles, be equivalent in emptying and dispersion properties to micronised (i.e. sub 10 micron) material.

The process for the production of finely divided nedocromil sodium, comprises atomising and drying a solution of nedocromil sodium and collecting some or all of the particles which have the desired properties, e.g. which are below 60, preferably below 40, more preferably below 30 and especially below 20 microns in diameter. The particles are preferably of the sizes given above.

Any suitable form of atomiser can be used. Atomisation results from an energy source acting on liquid bulk. Resultant forces build up to a point where liquid break-up and disintegration occurs and individual spray droplets are created. The different atomisation techniques available concern the different energy forms applied to the liquid bulk. Common to all atomisers is the use of energy to break-up liquid bulk. Centrifugal, pressure and kinetic energy are used in common forms of atomiser. Sonic and vibratory atomisers are also used. Specific atomisers which may be mentioned include rotary atomisers, e.g. those involving vaned wheels, vaneless discs, cups, bowls and plates; pressure atomisers, e.g. those involving pressure nozzles, centrifugal pressure nozzles, swirl chambers and grooved cores; kinetic energy or pneumatic atomisers, e.g. those involving two or three fluids, or internal or external mixing; and sonic energy nozzles, e.g. involving sirens or whistles. We prefer to use kinetic or pneumatic energy atomisers particularly two fluid pressure or syphon or sonic nozzle atomisers. In general two fluid pressure nozzles tend to produce powders having more desirable characteristics than two fluid syphon nozzles and two fluid pressure nozzles also tend to give more reproducible results and use less energy.

The atomiser can be used in a spray or flash drying apparatus.

The conditions of operation of the apparatus and storage of the solution (e.g. pH and temperature) should clearly not be such as to degrade nedocromil sodium, or introduce impurities, or biological contamination, into nedocromil sodium.

The spray drying apparatus preferably comprises the atomiser, a main chamber, one or more (e.g, two) cyclones, a bag filter and, if desired or necessary to maximise recovery, a terminal wet scrubber or electrostatic precipitator. The particle collection system is designed to capture the desired size range of particles and also to maximise the yield. All over and under size material may be recovered and recycled or put to other uses.

The solution of nedocromil sodium may be in any suitable solvent, e.g. water. The concentration of nedocromil sodium in the solvent may vary over a wide range, from 2 to 20, preferably 12 to 6, and especially 10 to 8% w/v. In general we prefer to use a high concentration of nedocromil sodium as the volume and energy requirements of the atomisation and drying process are thereby diminished. To avoid possible blockage of the atomisation device and to avoid the incorporation of unwanted impurities it is desirable to filter the solution immediately before it is passed to the atomiser. The particle size of the product tends to increase with concentration, but not rapidly, and in general concentration is not controlling with respect to particle size.

The temperature of the air inlet and outlet to the spray drier main chamber may vary over a wide range (the range being dependent on the solution through put and the final moisture content required) and suitable temperatures are 120°-200° C. In the case of aqueous solutions of nedocromil sodium, we have found that an air inlet temperature of from 140° to 185° C., preferably from 150° to 160° C., and an outlet temperature of from 50° to 100° C. and preferably of from 90° to 100° C. are suitable.

The temperature of the solution to be fed to the spray drier may vary with the solvent to be used. In general we prefer to use a temperature at which the solution can be stored for a long period in large batches without degradation. As high a temperature as possible commensurate with stability is desirable to reduce solution viscocity and provide energy to the drying process.

The air flow rate, direction into the spray drier, the temperature of the air and the rate of feed of solution to the spray drier can be optimised by simple experiment. All of the parameters in the spray drying process interrelate and can be adjusted to produce the desired product.

Gases other than air, e.g. nitrogen, can be used if desired. The use of an inert gas will be advantageous when an inflamable solvent is used. The gas used, e.g. air or nitrogen, may, if desired, be recycled to avoid loss of entrained nedocromil sodium and/or to conserve energy and the inert gas.

The particle size of the product will be set by the concentration of the feed solution, the rate of feed to the spray drier, the means of atomising the solution, e.g. the type of atomiser and the pressure of the air, and solution to be dried, the temperature and temperature gradient within the drier and, to a small extent, the air flow in the drier. The particle size and air flow will then dictate where the desired product is collected and the means of collection.

The particle size of the product tends to remain fairly constant with liquid flow rate through the atomiser, but to decrease with increasing air pressure up to a limiting pressure, e.g. of about 7 kg $cm^{-2}$. The range of air pressures suitable will naturally depend on the atomisation device used, but we have found that air pressures of from about 4 kg $cm^{-2}$ to 6 kg $cm^{-2}$ are in general effective, e.g. with a 0.4 mm orifice syphon two fluid nozzle. In order to achieve reproducible results we prefer to maintain a constant air flow to the dryer and appropriate air flow control devices may be used if desired.

The cyclone or cyclones used to collect the dried particles are of conventional design, but adapted to collect finer particles than is normal. Thus the pressure differential across the cyclones, the combination of two or more cyclones and the design of the particular cyclones used may be adjusted to enable capture of the fine particles. The bag filter used to collect the finest material is of conventional design and is readily available. The filter medium within the bag filter preferably has a high capture efficiency for particles of approximately 0.5 microns in diameter and greater. A particularly suitable medium is a polytetrafluoroethylene membrane supported on a polypropylene or polyester cloth, e.g. a needle felt cloth. Any electrostatic precipitator, or wet scrubber, used will also be of conventional design.

The product may be classified, e.g. sieved or air classified, to remove over and under sized material. The over and under sized material may be recycled or used for other purposes.

The final product may be put up in any suitable form of container such as a capsule or cartridge. Where it is desired to use the product in association with other ingredients such as colourants, sweeteners or carriers such as lactose, these other ingredients may be admixed with the particles of the invention using conventional techniques or may be incorporated in the solution to be spray dried. We prefer the particles of the invention to contain medicament and water only.

According to our invention we also provide a method of application of nedocromil sodium, to a patient by way of inhalation, the medicament being dispersed into an air stream, characterised in that an opened, e.g. pierced, container, e.g. capsule, containing particles according to the invention is rotated and vibrated in an air stream which is inhaled by the patient. The rotation and vibration may conveniently be produced by any one of a number of devices, e.g. the device of British Patent Specification No. 1,122,284.

The particles according to the invention may also be used in pressurised aerosol formulations (together with propellant gases, e.g. a mixture of two or more of propellants 11, 12 and 114, preferably with a surface active agent, e.g. sorbitan trioleate).

From another aspect the invention also provides a capsule, cartridge or like container containing particles according to the invention, optionally in association with other particles. We prefer the container to be loosely filled to less than about 80% by volume, preferably less than about 50% by volume, with the particles of the invention. The particles are preferably not compacted into the container. We prefer the container, e.g. capsule, to contain from 10 to 30 mg, e.g. about 20 mg, of the particles of nedocromil sodium.

According to the invention we also provide a finely divided inhalation formulation of nedocromil sodium comprising a therapeutically effective proportion of individual particles comprising nedocromil sodium and capable of penetrating deep into the lung, characterised in that a bulk of the particles which is both unagglomerated and unmixed with a coarse carrier, is sufficiently free flowing to be filled into capsules on an automatic filling machine and to empty from an opened capsule in an inhalation device, some of the particles being of dented spherical shape or toroidal and the permeametry: BET ratio of the particles being in the range of 0.5 to 1.0.

The invention will now be illustrated by the following Examples

EXAMPLE 1

Nedocromil sodium was dissolved in water to a concentration of between 5 and 10% w/v. The solution was spray dried in a Buchi mini spray dryer type 190 (Buchi is a trademark) using a feed flow rate of 10 ml/min. An air inlet temperature of 151° to 153° C. was used and the air outlet temperature was 85° to 90° C.

A powder was collected which had a loose bulk density of 0.38 g/cm$^3$ and a packed bulk density of 0.54 g/cm$^3$. The moisture content of the powder, which was determined by heating the powder to 120° C., was in the range 8.6 to 10.6% w/w.

EXAMPLE A

Nedocromil sodium according to the invention was filled into hard gelatin capsules and single stage liquid impinger tests were carried out. The single stage liquid impinger is a modified version of the multistage liquid impinger described in British Patent Specification No 1081881. The modified impinger is described in British Patent No 2105189.

The capsules were each filled with 20 mg of nedocromil sodium according to the invention. A dispersion range of 8 to 14% w/w was recorded and 80% by weight of the material had emptied from the capsule.

We claim:

1. Finely divided nedocromil sodium comprising a therapeutically effective proportion of individual parties of uniform shape capable of penetrating deep into the lung, said particles being both unagglomerated and unmixed with a coarse carrier, sufficiently free flowing to be capable of being filled into capsules on an automatic filling machine and to empty from an opened capsule in an inhalation device, and having a permeametry:BET ratio of from 0.5 to 1.0, said particles being prepared by atomizing and drying a solution of nedocromil sodium in a kinetic or pneumatic energy atomizer.

2. Nedocromil sodium according to claim 1 characterized in that the particles have a permeametry:BET ratio of from 0.6 to 1.0.

3. Nedocromil sodium according to claim 1 characterized in that it possesses a particle density of from about 1.3 to 1.8 g/cm$^3$.

4. Nedocromil sodium according to claim 3 characterised in that it possesses a particle density of from 1.4 to 1.7 g/cm$^3$.

5. Nedocromil sodium according to claim 1 characterised in that it has a loose bulk density of greater than 0.3 g/cm$^3$.

6. Nedocromil sodium according to claim 1 characterised in that it has a packed bulk density of from 0.5 to 1.0 g/cm$^3$.

7. Nedocromil sodium according to claim 1 characterised in that it has a moisture content of from 8.0 to 14.0% w/w.

8. Nedocromil sodium according to claim 7 characterised in that it has a moisture content of from 8.0 to 11.0% w/w.

9. Nedocromil sodium according to claim 1 characterised in that each individual particle comprises the active ingredient and a diluent.

10. Nedocromil sodium according to claim 1 characterised in that at least 80% by weight of the particles are of less than 60 microns in diameter.

11. Nedocromil sodium according to claim 10 characterised in that more than 90% of the drug particles are less than 60 microns in diameter.

12. Nedocromil sodium according to claim 1 characterised in that the particles are in admixture with two or more propellants in a pressurised aerosol formulation.

13. A method of application of nedocromil sodium according to claim 1 to a patient by way of inhalation characterised in that an opened container containing nedocromil sodium is rotated and vibrated in an air stream which is inhaled by the patient.

14. A capsule, cartridge or like container containing particles of nedocromil sodium according to claim 1.

15. A container according to claim 14 containing nedocromil sodium in association with one or more colourants, sweeteners or carriers.

16. A container according to claim 14 which is loosely filled to less than 80% by volume.

17. A container according to claim 14 containing from 10 to 30 mg of particles of nedocromil sodium.

18. A finely divided inhalation formulation of nedocromil sodium comprising a therapeutically effective proportion of individual particles comprising nedocromil sodium and capable of penetrating deep into the lung, characterized in that a bulk of the particles which is both unagglomerated and unmixed with a coarse carrier, is sufficiently free flowing to be filled into capsules on an automatic filling machine and to empty from an opened capsule in an inhalation device, some of the particles being of dented spherical shape or toroidal and the permeametry: BET ratio of the particles being in the range of from 0.5 to 1.0, said particles being prepared by atomizing and drying a solution of nedocromil sodium in a kinetic or pneumatic energy atomizer.

* * * * *